(12) United States Patent
Haidukewych

(10) Patent No.: US 7,524,334 B2
(45) Date of Patent: Apr. 28, 2009

(54) TIBIAL TRAY FOR TOTAL KNEE ARTHROPLASTY

(76) Inventor: George J. Haidukewych, 15301 Bursley, Tampa, FL (US) 33647

( * ) Notice: Subject to any disclaimer, the term of this patent is extended or adjusted under 35 U.S.C. 154(b) by 707 days.

(21) Appl. No.: 10/998,887

(22) Filed: Nov. 29, 2004

(65) Prior Publication Data
US 2006/0116772 A1 Jun. 1, 2006

(51) Int. Cl.
A61F 2/38 (2006.01)

(52) U.S. Cl. .................. 623/20.32; 623/20.34

(58) Field of Classification Search ... 623/20.32–20.34, 623/20.21, 23.44
See application file for complete search history.

(56) References Cited

U.S. PATENT DOCUMENTS

| 4,822,362 | A | 4/1989 | Walker et al. | |
| 5,092,895 | A * | 3/1992 | Albrektsson et al. | 623/20.3 |
| 5,282,866 | A | 2/1994 | Cohen et al. | |
| 5,356,414 | A | 10/1994 | Cohen et al. | |
| 5,509,934 | A | 4/1996 | Cohen et al. | |
| 5,658,341 | A | 8/1997 | Delfosse | |
| 5,683,469 | A | 11/1997 | Johnson et al. | |
| 5,976,147 | A | 11/1999 | LaSalle et al. | |
| 6,159,216 | A | 12/2000 | Burkinshaw et al. | |
| 6,258,127 | B1 * | 7/2001 | Schmotzer | 623/20.32 |
| 6,494,914 | B2 | 12/2002 | Brown et al. | |
| 6,506,216 | B1 | 1/2003 | McCue et al. | |
| 6,620,198 | B2 | 9/2003 | Burstein et al. | |
| 6,702,821 | B2 | 3/2004 | Bonutti | |
| 7,364,589 | B2 * | 4/2008 | Eisermann | 623/17.15 |
| 2003/0055509 | A1 | 3/2003 | McCue et al. | |
| 2003/0060884 | A1 | 3/2003 | Fell et al. | |
| 2003/0100953 | A1 | 5/2003 | Rosa et al. | |
| 2004/0019384 | A1 | 1/2004 | Kirking et al. | |
| 2004/0030397 | A1 | 2/2004 | Collazo | |
| 2004/0073315 | A1 | 4/2004 | Justin et al. | |

* cited by examiner

Primary Examiner—William H. Matthews
Assistant Examiner—Suba Ganesan
(74) Attorney, Agent, or Firm—David W. Pettis, Jr.

(57) ABSTRACT

An improved one piece tibial tray uniquely characterized by its construction including an asymmetric keel extending from the bottom of the tibial tray base plate, whereby insertion of the tray during arthroplasty may be accomplished with a smaller than normal incision, enhancing the efficacy and safety of the surgical procedure. A fin on either or both sides of the asymmetric fin may be provided for enhanced stability of the tray.

8 Claims, 5 Drawing Sheets

TIBIAL TRAY FOR TOTAL KNEE ARTHROPLASTY

BACKGROUND OF THE INVENTION

1. Field of the Invention

The present invention relates to an improved tibial tray that is positioned on the patient's tibia for joint replacement in a total knee arthroplasty. The improved tibial tray of this invention is of a unitary construction and comprises a unique, asymmetric keel that permits insertion through a relatively smaller incision.

2. Description of the Prior Art

Total knee arthroplasty is a common procedure performed worldwide. This procedure traditionally requires wide exposure of the distal femur and proximal tibia in order to permit appropriate preparation of the bone surfaces for implanting the components. Most implants performed today in the United States are cemented in place with polymethylmethacrylate cement. Extraneous cement is traditionally cleaned, requiring additional exposure of the femur and tibia to ensure sufficient removal and to prevent potential third body debris.

Over the past several years there has been a movement toward less invasive techniques for total knee arthroplasty. These less invasive techniques typically involve smaller incisions, less disruption of the musculature of the knee, and decreased visualization when compared to that of "traditional" total knee arthroplasty. One of the major technical hurdles in performing an accurate, minimally invasive total knee arthroplasty is obtaining adequate exposure in order to seat the currently available components, particularly the state-of-the-art tibial trays.

Traditionally, the tibial tray is cemented in place and has a relatively large keel, or a depending stem, used to control angular and rotational forces that are imparted to the tibial tray by the knee joint. Because of the size of such keels or stems today, the proximal tibia must be circumferentially exposed in order to allow appropriate preparation of the bone and seating of the implant. This requires subluxation of the tibia anteriorly and clearance of the posterior lateral femoral condyle to prevent iatrogenic fracture or improper seating of the components.

Furthermore, as the tibial tray is cemented in place, the most common method of prosthetic fixation, additional exposure is also necessary to debride cement as it extrudes from under the tray as the tray is forced into position. Even when traditional large incisions are used, the procedure is challenging. With the advent of minimally invasive techniques, another level of difficulty is added because the components must be placed through smaller incisions in the patient's skin.

One means for solving the problem is shown in prior patented devices as modular tibial trays. By use of the term "modular" it is meant that the trays include a keel or stem that is separate from the tibial base plate. In order to facilitate minimally invasive insertion, the keel or stem is inserted into the tibia, and the base plate is attached thereto. However, a relatively larger incision is still necessary for insertion of the keel or stem, and modular devices are frequently more expensive than unitary devices, and the parts may not mate properly. Furthermore, intraoperative assembly is necessary, and this may prove to be more difficult when working through small incisions. Finally, modularity can result in modular interface fatigue fracture, fretting, and/or debris generation that can compromise the effective life of the arthroplasty.

SUMMARY OF THE INVENTION

The present invention relates to an improved tibial tray used for total knee arthroplasty wherein the improved tray comprises a base plate having a top surface and a bottom surface, and an asymmetric keel depending from the bottom surface and, in a preferred construction, a pair of opposed fins depending from the bottom surface and integral with opposed sides of the keel. The asymmetric configuration of the keel not only permits insertion through a smaller incision, but also tends to expel cement toward the surgeon as the tray is inserted in place, enhancing the ease with which excess cement may be removed. The fins provide strength and rotational stability to the tray once it has been placed.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

DETAILED DESCRIPTION

Figure 1:
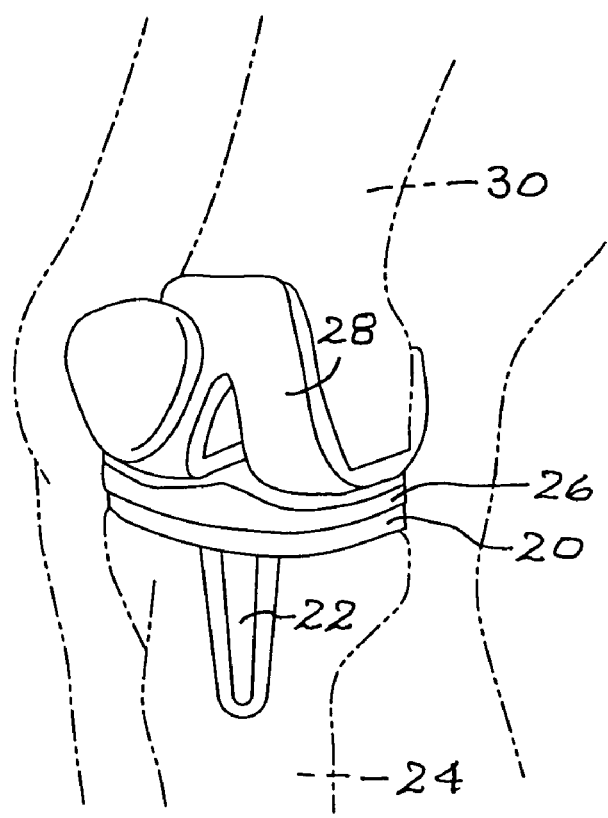
FIG. 1 is an illustration of state-of-the-art total knee arthroplasty.

Before providing a detailed description of the preferred embodiments of the present invention, attention is invited to the view of FIG. 1 wherein a prior art total knee arthroplasty is indicated. As shown in the view of FIG. 1, a prior art tibial tray is shown at 20 and includes a prior art stem 22 which has been operatively placed within the prepared tibia 24. A prior art condylar bearing surface 26 is provided above prior art tibial tray 20, and a prior art femoral component 28 is shown in operative attachment to femur 30.

In order to position prior art tibial tray 20 and its stem 22 within tibia 24, rather large exposure of the proximal tibia and in-line axial impaction of the prior art tibial tray 20 is required. Because cement is typically used to fix tibial tray 20 and stem 22 to the tibia 24, excess cement will tend to be expelled circumferentially as tray 20 is positioned.

Figure 2:
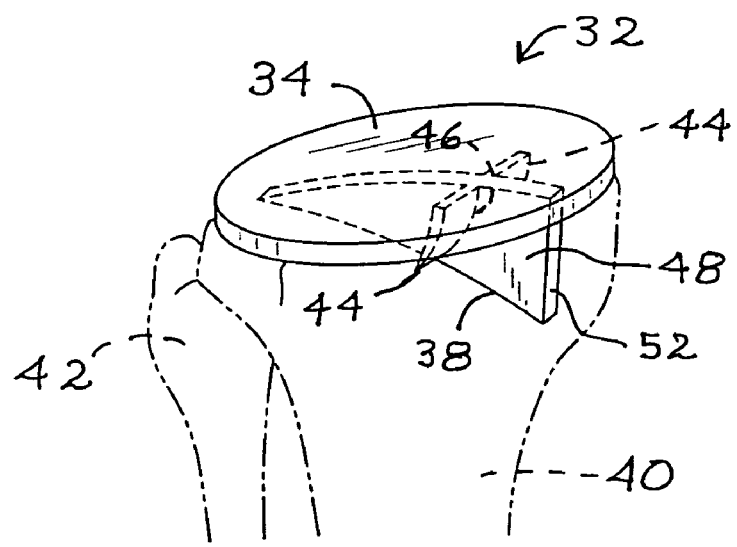
FIG. 2 depicts a first embodiment of the improved tibial tray of this invention with portions of the patient's tibia and fibula shown in phantom.
Figure 3:
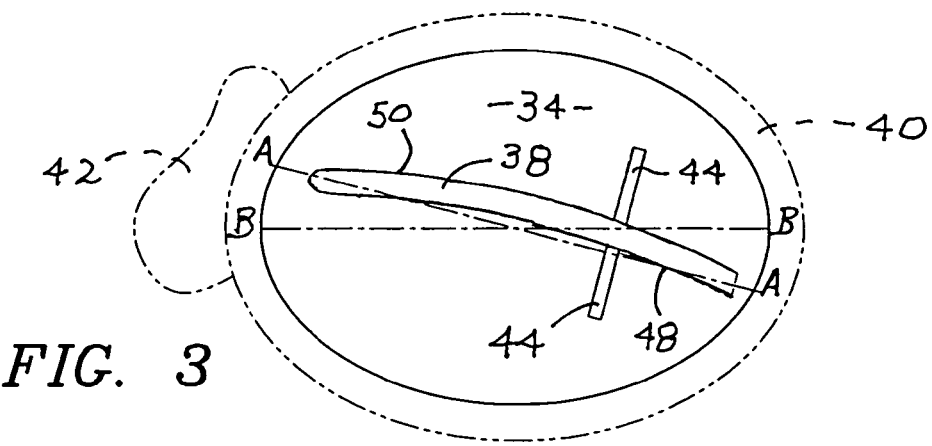
FIG. 3 is a superior plan view of the embodiment of FIG. 2 (patient's right leg).

Embodiments of the improved tibial tray of this invention are shown in the remaining figures, and attention is first invited to the view of FIG. 2 wherein a first embodiment of the improved tibial tray is generally indicated as 32. Tibial tray 32 includes a top surface 34 and a bottom surface 36. Integrally formed on bottom surface 36 and extending downwardly therefrom is asymmetric keel 38. Shown in phantom in the view of FIG. 2 is an anterior view of the patient's tibia 40 and fibula 42. Also shown in the view of FIG. 2 are a pair of opposed fins 44. Fins 44 are integrally formed on bottom surface 36 and extend downwardly, each including a keel edge 46 that is integral with a corresponding first side 48 and second side 50 of asymmetric keel 38. The view of FIG. 3 is a superior plan illustration of placement of tibial tray 32, as shown in the view of FIG. 2. The view of FIG. 4 illustrates placement of the improved tibial tray on the patient's other leg.

Figure 4:
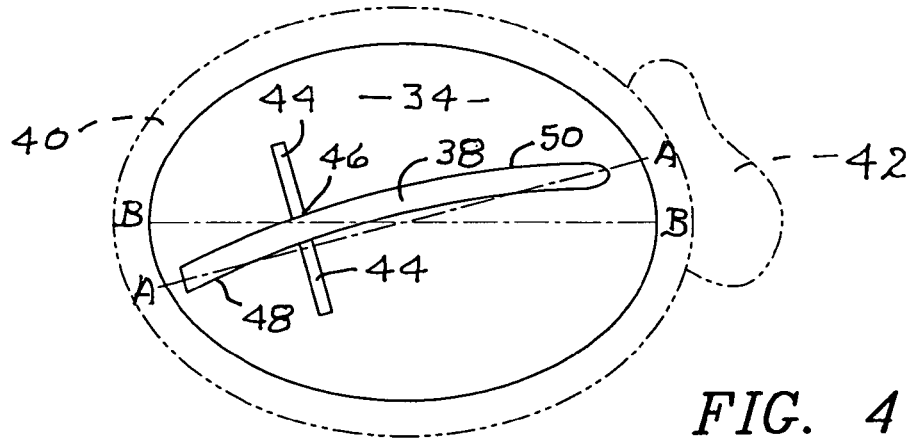
FIG. 4 is a superior plan view similar to that of FIG. 3 (patient's left leg).

As can be seen in the views of FIGS. 2-4, proper placement of the improved tibial tray 32 of this invention calls for positioning the tray 32 such that the major depth of asymmetric keel 38, indicated by edge 52, is anchored into tibia 40 where the bone is more dense.

Not only is asymmetric keel 38 "deeper" at edge 52, tapering to its opposed end, but also asymmetric keel 38 may be curved as clearly seen in the views of FIGS. 3 and 4 in order to provide even greater stability for the final total knee arthroplasty. Dotted line A-A depicts the curvature of asymmetric keel 38, and dotted line B-B illustrates the medial placement of improved tibial tray 32 on the patient's tibia 40.

Figure 6:
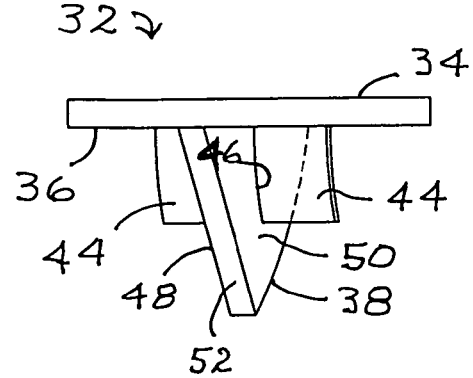
FIG. 6 is an oblique elevation similar to that of FIG. 5 showing curved fins.

Referring once again to the view of FIGS. 2 and 6, one can see that in this embodiment for improved tibial tray 32 each of the fins 44 may curve away from edge 52, and each of the fins 44 are tapered to ease insertion.

Figure 5:
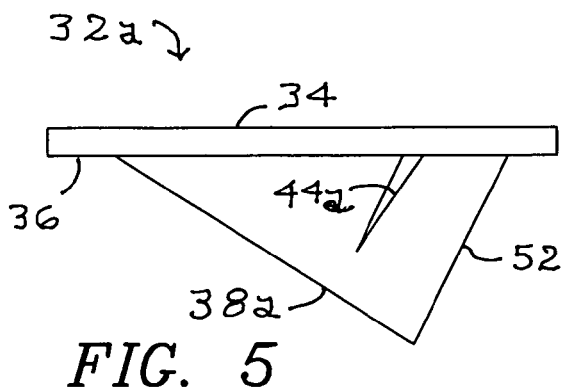
FIG. 5 is a side elevation of a second embodiment for the improved tibial tray of this invention.

The view of FIG. 5 depicts a second embodiment for the improved tibial tray of this invention, generally indicated as 32a. In this embodiment for tibial tray 32a, fins 44a are not curved, and asymmetric keel 38a is not curved. Furthermore, the embodiment for tibial tray 32a may include a single fin 44a, and the use of a single fin may be employed in all embodiments of this invention.

Figure 8:
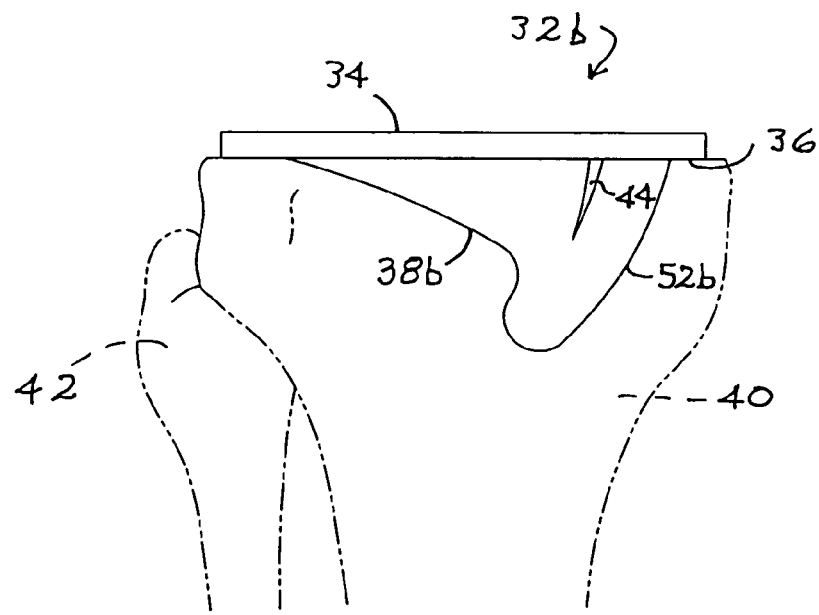
FIG. 8 depicts a third embodiment for the tibial tray of this invention in a view similar to that of FIG. 3.

Turning to the view of FIG. 8, a third embodiment for the improved tibial tray is generally indicated as 32b. As can be clearly seen in the view of FIG. 8, asymmetric keel 38b is of a curved configuration, rather than angular. Of course, asymmetric keel 38b still includes an edge 52b that extends downwardly from bottom surface 36 to a maximum depth within tibia 40. In this embodiment of improved tibial tray 32b, asymmetric keel 38b is preferably curved as is keel 38, but may be straight as described with regard to keel 38a.

Figure 7:
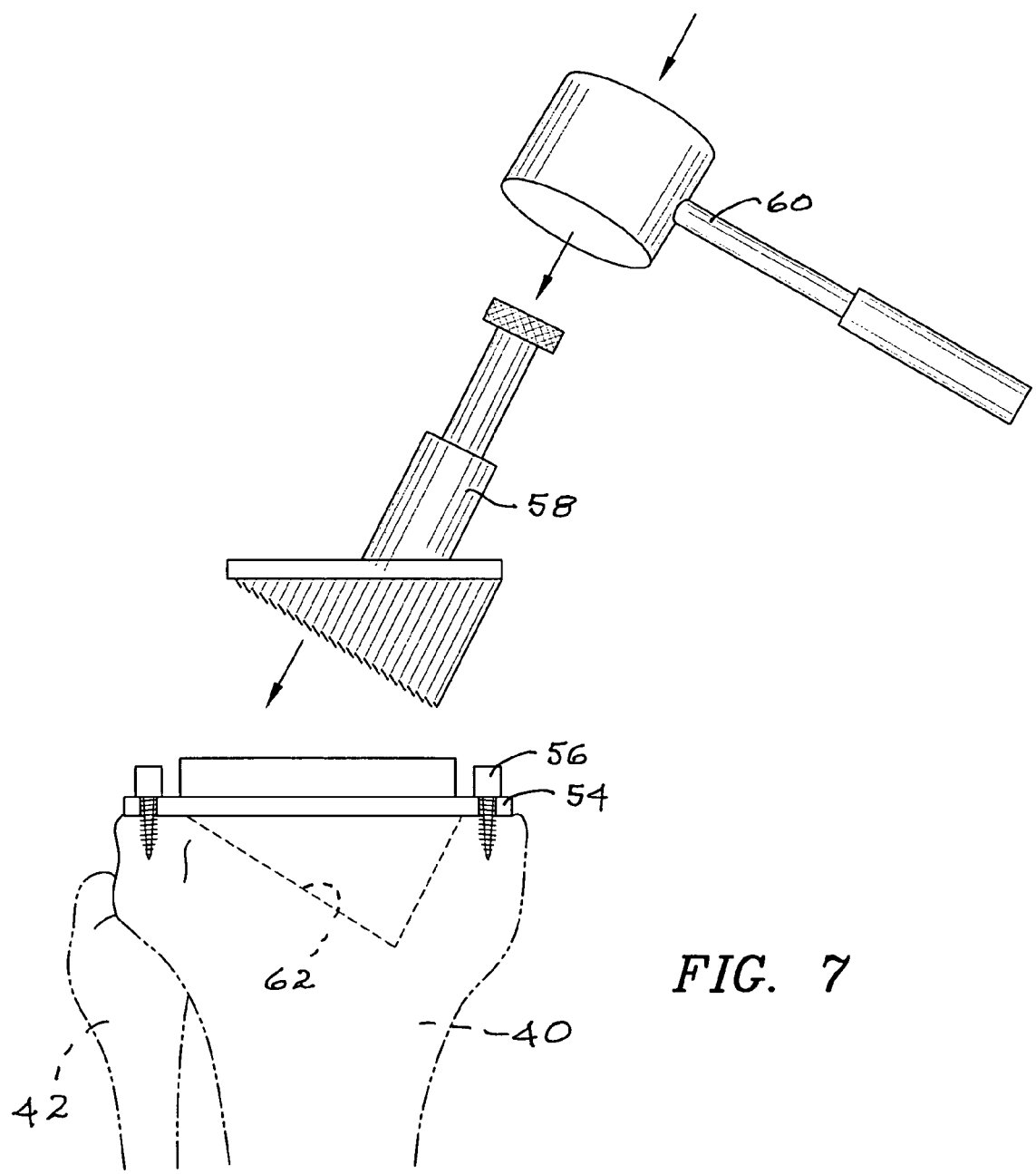
FIG. 7 illustrates preparation of the patient's tibia for insertion of the improved tibial tray of this invention.

The view of FIG. 7 is provided to illustrate preparation of tibia 40 for insertion and attachment of the improved tibial tray of this invention. A trial tray 54 is attached to tibia 40 as by pins 56, then a chisel 58 is repeatedly struck by mallet 60 to form a void 62 for receiving the asymmetric keel of the improved tibial tray. It is, of course, to be understood that chisel 58 would be dimensioned and configured to provide a void 62 corresponding to the configuration of the chosen asymmetric keel.

Figures 9, 10:
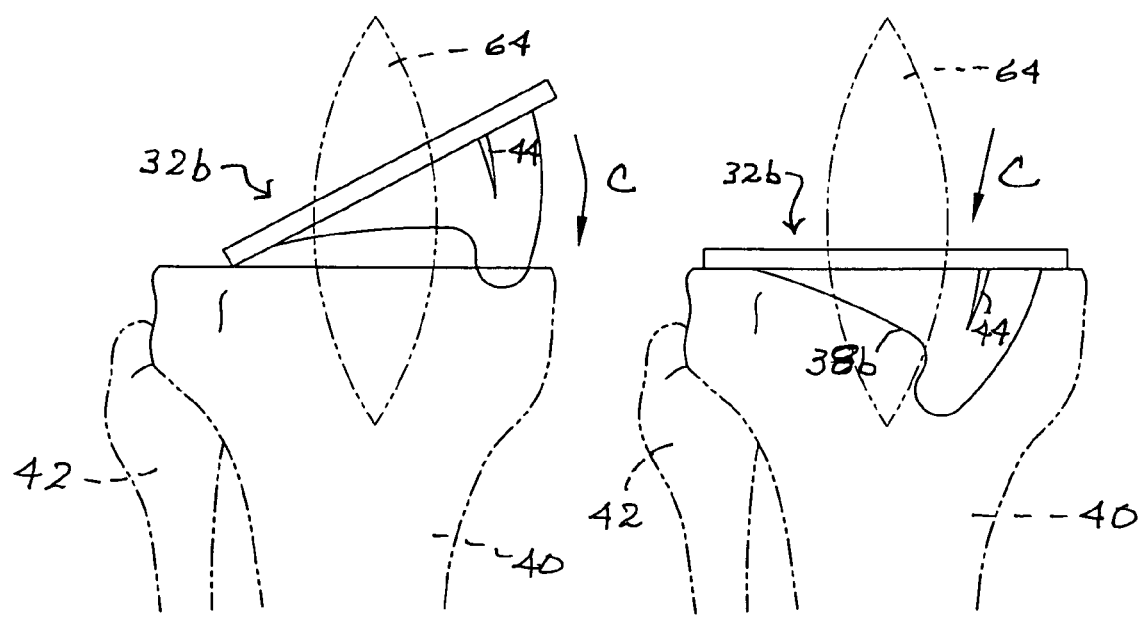
FIG. 9 illustrates the beginning of insertion of the embodiment of FIG. 8.
FIG. 10 illustrates final placement of the embodiment of FIG. 8.

The views of FIGS. 9 and 10 depict insertion of improved tibial tray 32b after preparation of the patient's tibia 40, as represented in the view of FIG. 7. The phantom oval shown in each of FIGS. 9 and 10 schematically represents a minimal incision 64 for placement of tray 32b.

Figure 11:
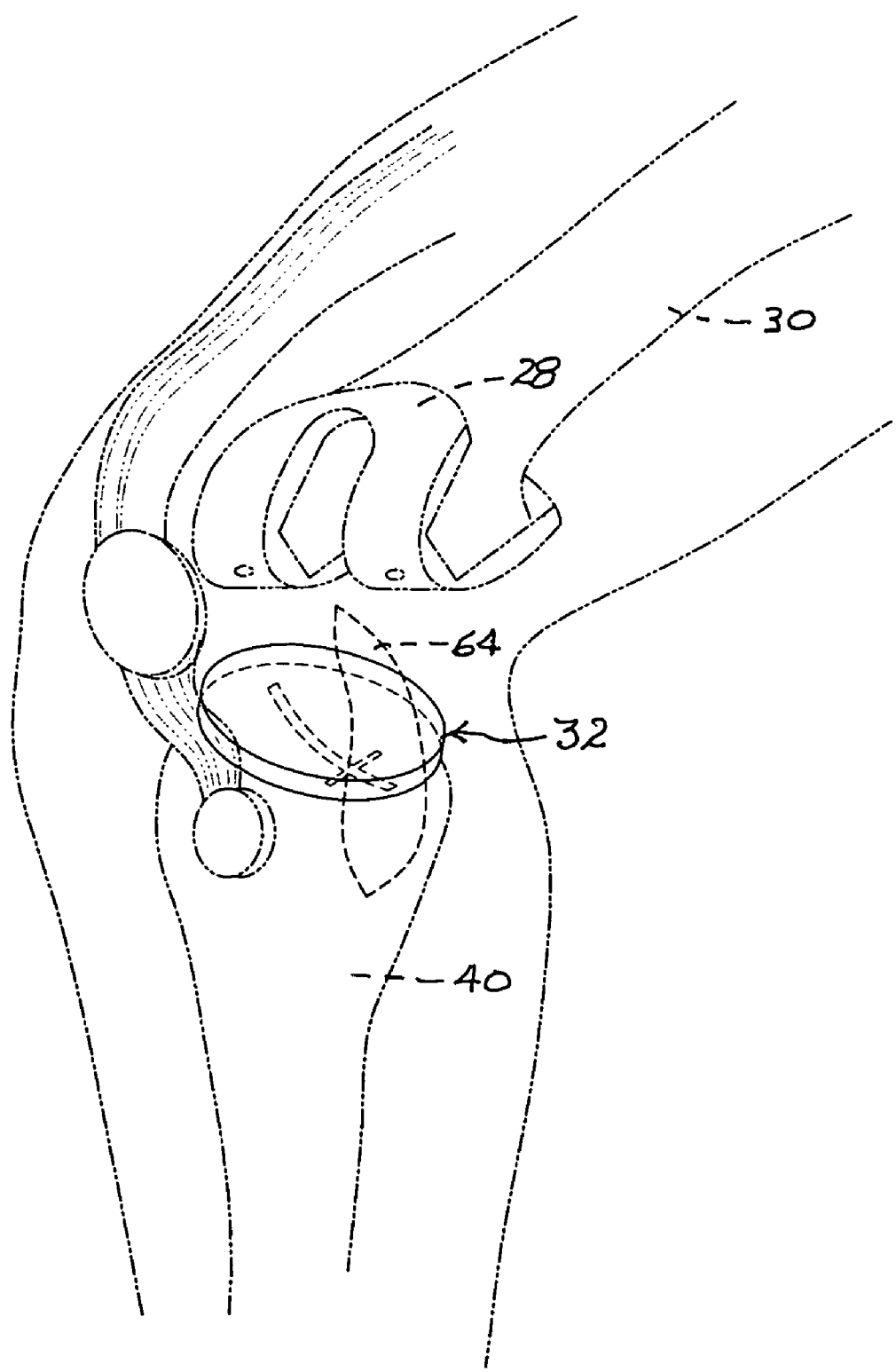
FIG. 11 is a view similar to that of FIG. 1 illustrating total knee arthroplasty using the improved tibial tray of this invention Similar reference characters refer to similar parts throughout the several views of the drawings.

As indicated by directional arrows C, tray 32b is inserted through incision 64 and rotated downwardly for final placement. It is primarily the shape of asymmetric keel 38b which permits insertion through a minimal incision 64. It can also be appreciated that as tray 32b is inserted into the prepared tibia 40, cement (not shown) will extravasate toward the surgeon, rather than away from the surgeon. This necessarily enhances the ease with which excess cement may be removed. FIG. 11 schematically depicts the completed total knee arthroplasty using the improved tibial tray 32 of this invention.

Thus, the unitary improved tibial tray of this invention, including embodiments 32, 32a, and 32b, is not only more easily inserted by the surgeon with minimally invasive incisions, but also simplifies manufacturing costs. The slope of the asymmetric keel allows the surgeon to insert the posterolateral portion of the tray first, with the advantageous result that the cement mantle is then compressed from posterolateral to anteromedial as the tray is tipped and rotated into correct position and impacted for final placement. As indicated above, this allows the cement to extravasate toward the surgeon, facilitating intraoperative cleaning. By virtue of the larger medial portion of the asymmetric keel, appropriate rotational and angular stability of the tray is maintained. Of course, this is also enhanced by the presence of at least one fin.

It will thus be seen that the objects set forth above, among those made apparent from the preceding description, are efficiently obtained and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An improved tibial tray for total knee arthroplasty, said tibial tray comprising: a tibial base plate comprising a top surface and a bottom surface, said tibial base plate further comprising an asymmetric keel integrally formed on said tibial base plate and depending from said bottom surface, said asymmetric keel comprising a first side and a second side; and said tibial base plate further comprising at least one fin integrally formed on said tibial base plate and depending from said bottom surface, said fin comprising a keel edge that is integrally attached to one of said first and second sides of said asymmetric keel, said first side and said second side of said asymmetric keel each defining non-planar curved surfaces that are substantially parallel to each other.

2. A tibial tray as in claim 1 wherein said at least one fin defines a plane that is substantially normal to said one of said first and said second sides of said asymmetric keel at said keel edge.

3. A tibial tray as in claim 2 wherein said asymmetric keel further comprises a bottom edge distal from said bottom surface, said bottom edge defining a curved line.

4. A tibial tray as in claim 2 wherein said asymmetric keel further comprises a bottom edge distal from said bottom surface, said bottom edge defining a straight line.

5. A tibial tray as in claim 4 comprising a pair of said fins, each one of said pair depending from said bottom surface and one of said pair comprising a keel edge that is integral with said first side of said asymmetric keel and the other of said pair comprising a keel edge that is integral with said second side of said asymmetric keel.

6. A tibial tray as in claim 5 wherein each one of said pair of fins defines a curved surface extending outwardly from said asymmetric keel.

7. A tibial tray as in claim 6 wherein said asymmetric keel further comprises a bottom edge distal from said bottom surface, said bottom edge defining a curved line.

8. A tibial tray as in claim 5 wherein one of said pair of said fins defines a plane that is substantially normal to said first side of said asymmetric keel at said keel edge and the other of said pair of said fins defines a plane that is substantially normal to said second side of said asymmetric keel at said keel edge.

* * * * *